United States Patent
Fulton et al.

(10) Patent No.: US 10,722,178 B2
(45) Date of Patent: Jul. 28, 2020

(54) METHOD AND APPARATUS FOR MOTION CORRECTION IN CT IMAGING

(71) Applicants: Western Sydney Local Health District, Westmead Sydney, NSW (AU); The University of Sydney, Sydney, NSW (AU); Katholieke Universiteit Leuven KU Leuven R&D, Leuven (BE)

(72) Inventors: Roger Fulton, Killara (AU); Johan Nuyts, Heverlee (BE); Tao Sun, Leuven (BE); Jung-Ha Kim, Wentworth Point (AU)

(73) Assignees: Western Sydney Local Health District (AU); The University of Sydney (AU); Katholieke Universiteit Leuven KU Leuven R&D (BE)

(*) Notice: Subject to any disclaimer, the term of this patent is extended or adjusted under 35 U.S.C. 154(b) by 110 days.

(21) Appl. No.: 15/608,666

(22) Filed: May 30, 2017

(65) Prior Publication Data

US 2017/0340287 A1 Nov. 30, 2017

(30) Foreign Application Priority Data

May 30, 2016 (AU) ................. 2016902042

(51) Int. Cl.
 *A61B 6/00* (2006.01)
 *A61B 5/00* (2006.01)
 *G06F 3/0484* (2013.01)
(52) U.S. Cl.
 CPC .......... *A61B 5/721* (2013.01); *G06F 3/04847* (2013.01)

(58) Field of Classification Search
 CPC .. A61B 5/00; A61B 5/721; A61B 6/00; A61B 6/52; A61B 6/5205; A61B 6/5211; A61B 6/5258; A61B 6/5264; G06F 3/0484; G06F 3/04847; G06T 2207/00; G06T 2207/10081; G06T 2207/10116
 USPC .................. 378/4, 15, 901; 382/131
 See application file for complete search history.

(56) References Cited

FOREIGN PATENT DOCUMENTS

WO 2017071956 A1 5/2017

OTHER PUBLICATIONS

A. Kyme et. al, "Markerless Motion Tracking of Awake Animals in Positron Emission Tomography", IEEE Trans. Med. Imaging, vol. 33, No. 11, pp. 2180-2190, Nov. 2014.
M. J. Ackerman, "The Visible Human Project", Proceedings of the IEEE, vol. 86, No. 3, pp. 504-511, Mar. 1998.
(Continued)

*Primary Examiner* — Jurie Yun
(74) *Attorney, Agent, or Firm* — St. Onge Steward Johnston & Reens, LLC (57) ABSTRACT

A method for the reduction of motion artifacts in CT imaging, the method including the steps of: (a) reconstructing from the raw CT data an initial estimate of the object of interest; (b) estimating the pose of the object at each projection angle; (c) undertaking a motion-corrected reconstruction from the measured projections, accounting for the pose changes estimated in (b) by employing a modified source/detector orbit that accounts for the object motion; (d) iterating steps (b)-(c) until a predetermined convergence criterion is met; and (e) making a final reconstruction of the required image size using the pose estimates obtained in the previous steps.

10 Claims, 6 Drawing Sheets

(56) References Cited

OTHER PUBLICATIONS

J. F. Barrett et. al, "Artifacts in CT: Recognition and Avoidance", Radiographics, vol. 24, No. 6, pp. 1679-1691, Nov.-Dec. 2004.

B. De Man et. al, "Distance-driven projection and backprojection in three dimensions", Phys. Med. Biol., vol. 49, pp. 2463-2475, May 19, 2004.

F. Fahmi et al, "Head movement during CT brain perfusion acquisition of patients with suspected acute ischemic stroke", Eur. J. Radiol., vol. 82, pp. 233✓ 2341, 2013.

R. R. Fulton et al., "Use of 3D reconstruction to correct for patient motion in SPECT", Phys. Med. Biol., vol. 39, pp. 563-574, 1994.

G. T. Gullberg et. al, "Estimation of geometrical parameters and collimator evaluation for cone beam tomography", Med. Phys., vol. 17, No. 2, pp. 264-272, Mar./Apr. 1990.

H. Yu et. al, "Data Consistency Based Rigid Motion Artifact Reduction in Fan-Beam CT", IEEE Trans. Med. Imaging, vol. 26, No. 2, pp. 249-260, Feb. 2007.

Jen-Bin Huang et al., "Pose determination of a cylinder using reprojection transformation", Pattern Recognition Letters, vol. 17, pp. 1089-1099, 1996.

H. M. Hudson et. al, "Accelerated Image Reconstruction Using Ordered Subsets of Projection Data", IEEE Trans. Med. Imaging, vol. 13, No. 4, pp. 601-609, Dec. 1994.

B. F. Hutton et. al, "A Hybrid 3-D REconstruction/Registration Algorithm for Correction of Head Motion in Emission Tomography", IEEE Trans. Nucl. Sci., vol. 49, No. 1, pp. 188-194, Feb. 2002.

J.-H. Kim et. al, "A rigid motion correction method for helical computed tomography (CT)", Phys. Med. Biol., vol. 60, No. 7, pp. 2047-2073, 2015.

Jung-Ha Kim, "The Estimation and Correction of Rigid Motion in Helical Computed Tomography", Discipline of Medical Radiation Sciences, Faculty of Health Sciences, The University of Sydney, Thesis submitted for the degree of Doctor of Philosophy, Jun. 29, 2016.

A Kingston et al., "Reliable automatic alignment of tomographic projection data by passive auto-focus", Med. Phys. vol. 38, No. 9, pp. 4934-4945, Sep. 2011.

Y Kyriakou et al., "Simultaneous misalignment correction for approximate circular cone-beam computed tomography", Phys. Med. Biol., vol. 53, pp. 6267-6289, 2008.

W Lu and T R Mackie, "Tomographic motion detection and correction directly in sinogram space", Phys. Med. Biol., vol. 47, pp. 1267-1284, Apr. 5, 2002.

Y. Nesterov, "A Method of Solving a Convex Programming Problem with Convergence Rate", Sov. Math. Dokl., vol. 27, No. 2, pp. 372-376, 1983.

P Noonan, et al., "Realtime Markerless Rigid Body Head Motion Tracking Using the Microsoft Kinect", IEEE Nucl. Sci. Symp. Med. Imaging Conf. Rec., pp. 2241-2246, 2012.

H. L. Pham et al., "Set-point control of robot end-effector pose using dual quaternion feedback", Robotics and Computer-Intregrated Manufacturing, vol. 52, pp. 100-110, 2018.

C J Ritchie et al., "Correction of Computed Tomography Motion Artifacts Using Pixel-Specific Back-Projection", IEEE Trans. Med. Imaging, vol. 15, No. 3, pp. 333-342, Jun. 1996.

C Rohkohl et al., "Improving best-phase image quality in cardiac CT by motion correction with MAM optimization", Med. Phys., vol. 40, No. 3, pp. 03190-1-031901-15, Mar. 2013.

S Ens et al., "Sinogram-Based Motion Detection in Transmission Computed Tomography", 4th European Conference of the International Federation for Medical and Biological Engineering: ECIFMBE 2008, pp. 505-508, 2008.

A. Savitzky et. al, "Smoothing and Differentiation of Data by Simplified Least Squares Procedures", Anal. Chem., vol. 36, pp. 1627-1639, Jul. 8, 1964.

Jakob M. Slipsager et al., "Markerless motion tracking and correction for PET, MRI, and simultaneous PET/MRI", PloS ONE, vol. 14, No. 4, Apr. 19, 2019.

T. Sun et. al, "Data-driven Rigid Motion Correction for Helical CT", Proc. of the 13th Int. Meeting on Fully Three-Dimensional Image Reconstruction in Radiology and Nuclear Medicine, Newport, RI, pp. 444-447, Jun. 2015.

Tao Sun, "Rigid Motion Correction for Head CT Imaging", KU Leuven, Biomedical Sciences Group, Faculty of Medicine, Department of Imaging and Pathology, Thesis for degreee of Doctor in Biomedical Sciences, Feb. 2018.

Wenli, Xu, and Zhang Lihua. "Pose estimation problem in computer vision." Proceedings of TENCON'93. IEEE Region 10 International Conference on Computers, Communications and Automation. vol. 2. IEEE, 1993.

Wikipedia, "Pose (computer vision)", https://en.wikipedia.org/w/index.php?title=Pose_(computer_vision)&oldid=902880740; last edited Jun. 21, 2019.

Z Yu et al., "Kinetic parameter reconstruction for motion compensation in transmission tomography", Proc. SPIE 7873, Computational Imaging IX, 78730T, Feb. 7, 2011.

METHOD AND APPARATUS FOR MOTION CORRECTION IN CT IMAGING

FIELD OF THE INVENTION

The present invention provides for systems and methods for the automated correction of motion artefacts in x-ray CT images created for medical and other applications.

BACKGROUND OF THE INVENTION

Any discussion of the background art throughout the specification should in no way be considered as an admission that such art is widely known or forms part of common general knowledge in the field.

One of the major sources of image artifacts in computed tomography (CT) is motion of the object of interest, which creates inconsistencies between acquired projections, leading to distortion and blurring when images are reconstructed. For example, in medical CT performed for diagnostic purposes, motion artifacts can lead to false diagnosis. Motion artifacts affect many medical CT medical imaging procedures, such as CT perfusion scans for suspected acute ischemic stroke. They are also a problem in cone beam imaging (for radiotherapy treatment verification), in dental CT, and in some industrial CT imaging applications. Head motion is a common problem in young patients who are often sedated or anesthetized to prevent motion. According to the latest available data, over 70 million medical CT scans are performed annually in the USA alone, of which approximately 10% are performed in children. Moreover, a recent survey of CT practice in developing countries revealed that about 75% of pediatric CT scans were of the head. Due to the relatively high radiation dose associated with CT scanning, it is undesirable to repeat the scan if motion occurs, particularly in children who have a much higher estimated lifetime risk of radiation-induced cancer than adults. In adults, head motion is a problem for patients suffering from claustrophobia or a mental or behavioral incapacity, and in patients with head trauma. In a recent study, head movements classified as moderate or severe were observed in 25% of 103 patients with acute ischemic stroke during CT brain perfusion scans.

In medical CT, a slight movement of the patient will lead to a reduction of spatial resolution, in severe cases resulting in corrupted images unsuitable for diagnosis or further processing. To reduce the likelihood of motion artifacts, medical CT manufacturers have made scanners faster by increasing the number of detector rows and the rate of rotation of the x-ray source and detector, which is not a complete solution. Several motion correction methods have been suggested in the literature, the majority of which are intended for circular cone beam CT (CBCT), and few studies have addressed motion correction for medical multi-slice CT (MSCT) systems. In the latter, the object is often translated axially at a constant speed while the source and detector rotate around it, creating a helical orbit. Motion correction is more tractable in CBCT as the entire object is normally in the field of view at all times. In contrast, with MSCT, the object is always truncated in axial direction, which complicates the application of analytical motion correction algorithms.

Assessment of the object motion is of considerable general interest in tomography. In the medical imaging field, a variety of methods have been applied to the estimation of head motion, including direct motion estimation using a camera system with visual markers or without markers. Artificial or anatomical landmarks can be also tracked in the image or projection domain. Indirect estimation methods have been proposed where motion is estimated through the minimization of errors in consistency conditions using projection moments, or by an iterative process using re-projected image information. Another approach has used similarity measures to quantify changes between projections to measure object motion. Previously, there has been some progress in applying rigid motion correction techniques to helical CT brain scans, by measuring the head motion with a Polaris system (Spectra, Northern Digital Inc, Waterloo, Canada).

Even with these techniques, errors are still visible in the resulting images. The possible reason is that there still is some residual unrecorded motion in each pose, caused by small errors in the pose measurements. "Pose" is a common term in the field, and is used to describe the position and orientation of the portion of the rigid object, e.g. subject/patient, being x-rayed for imaging. Accordingly, a change in a patient's head pose may have six parameters such as three linear translations (x, y, z) and three rotations (about axis x, y, z, for example). These residual, unrecorded changes in pose will result in 'jagged' artifacts which are most visible at the edge of the phantom.

It would be desirable to provide for improved processing of CT imagery to reduce the level of motion artifacts.

SUMMARY OF THE INVENTION

It is an object of the invention, in its preferred form to provide an improved form of reconstruction of CT images.

In accordance with a first aspect of the present invention, there is provided a method for the reduction of motion artifacts in a CT reconstruction, the method including the steps of: (a) reconstructing from the raw CT data, consisting of projection views acquired at a plurality of angles around the object, an initial estimate of the attenuation distribution within the object of interest; (b) estimating the pose (i.e., the position and orientation) of the object at each projection angle; (c) undertaking a motion corrected reconstruction from the measured projections, accounting for the pose changes estimated in (b); (d) iterating steps (b)-(c) until a convergence criterion is met; (e) performing a final reconstruction of diagnostic quality using the pose estimates obtained in the previous steps.

The step (b) preferably can include the minimization of a cost function including a difference measure of the measured projection image and an image produced by forward projection of the current estimate of the object in its currently estimated pose.

The step (c) includes forming a motion corrected image from the raw CT data, using a reconstruction algorithm that accounts for the motion estimated in step (b).

Figure 2:
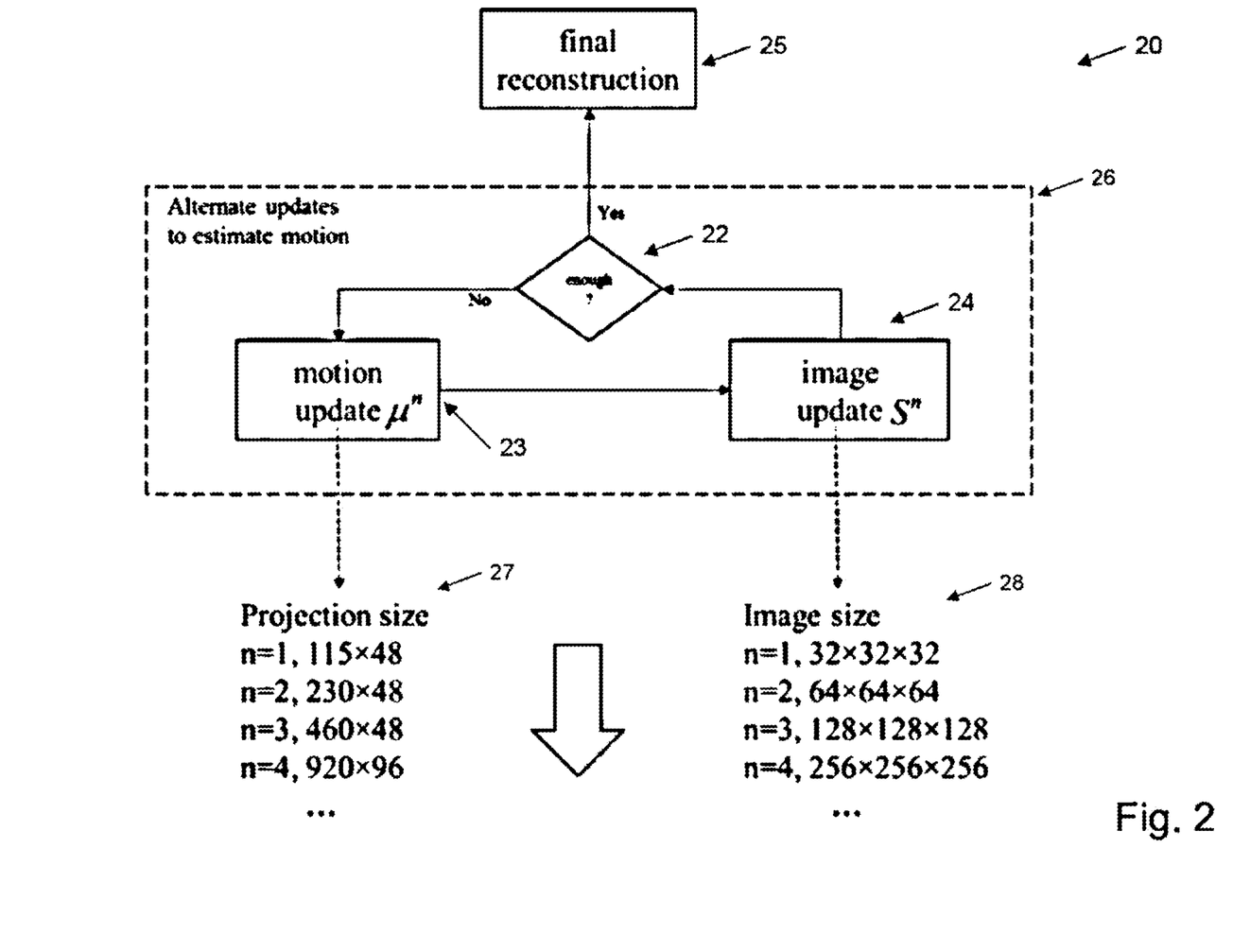
FIG. 2 illustrates a flow diagram of the general motion estimation scheme. μ is the update of the attenuation image, S is the update of the rigid transform, n is the iteration number. A multi-resolution scheme 27, 28 was applied to the motion estimation, increasing the sampling as the iteration number. The motion update uses the current estimate of the motion corrected image $\mu^n$, the image update uses the resulting motion estimate $S^n$ to produce an updated motion corrected image.

Preferably, the iterations (b)-(c) are performed across multiple resolutions of the helical CT image, with the multiple resolutions being of increasing fidelity as shown in FIG. 2.

In step (b), pose is estimated as a combination of three dimensional rotations and translations of the object of interest. In some embodiments, one of said translations is perpendicular to the detector and need not be estimated as it has a negligible effect on the measured CT projection image.

BRIEF DESCRIPTION OF THE DRAWINGS

Embodiments of the invention will now be described, by way of example only, with reference to the accompanying drawings in which:

In FIG. 2, the resolution is increased for every iteration n, but in practice, multiple iterations may be carried out at each resolution level.

DETAILED DESCRIPTION OF THE INVENTION

The preferred embodiments provide a data-driven method to iteratively correct for motion errors together with the reconstruction of CT images. In every iteration, an estimate of the motion is undertaken, view-by-view, which can then be used to create the modified source/detector orbit that would have been required to obtain the measured projections if the object remained stationary. Applying a reconstruction algorithm with the assumption that this modified orbit was followed during data acquisition rather than the true orbit provides an updated motion-corrected reconstruction. A multi-resolution scheme was used to speed up the convergence of the joint estimation of the motion and the motion-corrected reconstruction. The quality of the reconstructed images may be improved substantially after the correction. The motion correction method is applicable to helical CT, circular orbit CT, cone beam CT and dental CT. The method is particularly advantageous to helical CT as described below.

The approach has been found to reduce or eliminate the motion artifacts in CT reconstruction, and in particular, helical CT. The correction method was found to only need the measured raw helical scan data, hence it is called a 'data-driven' approach.

The Method

Figure 1:
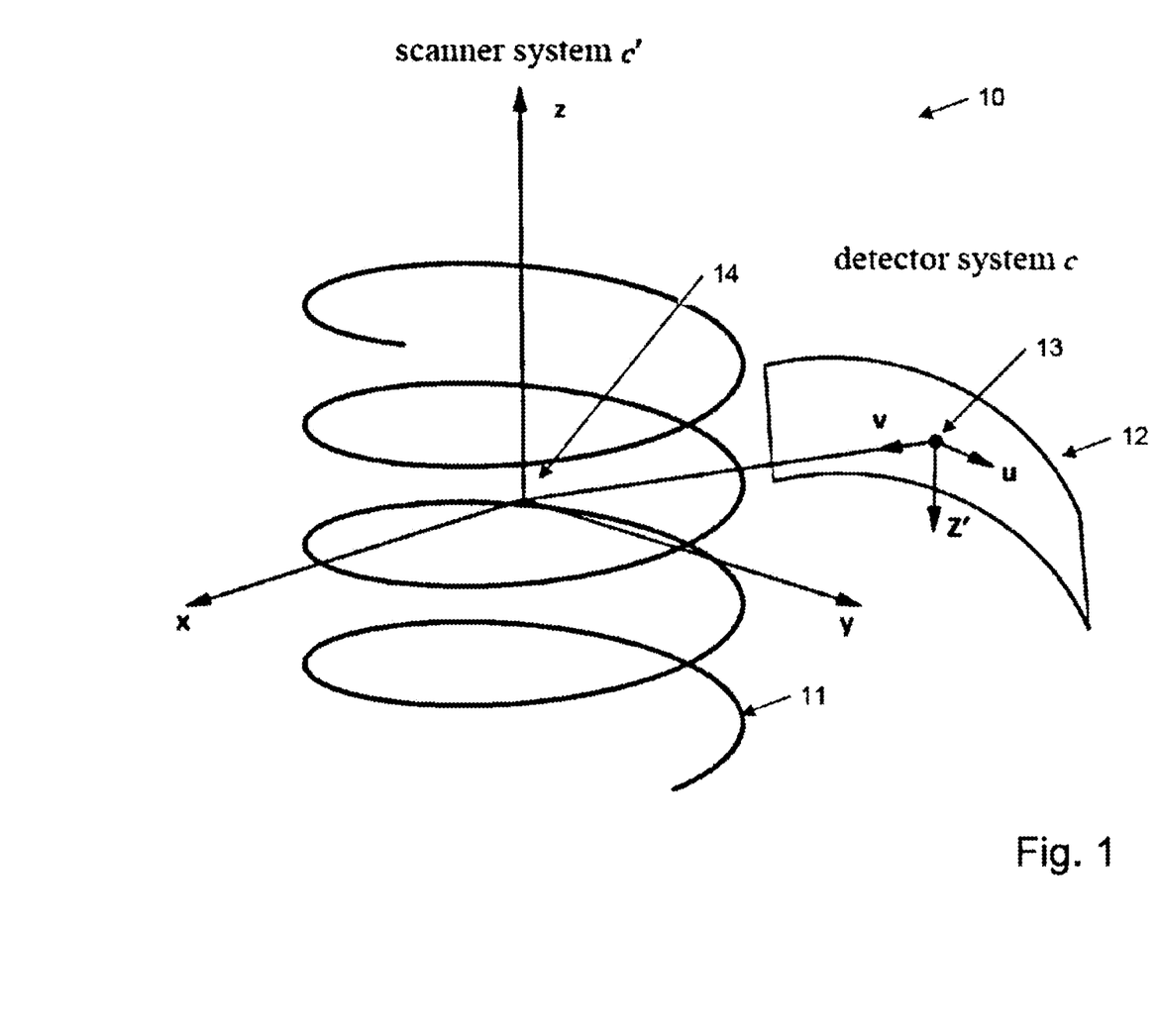
FIG. 1 illustrates schematically the scanner and detector coordinate systems on which motion correction is based.

Coordinate Systems: Turning initially to FIG. 1, there is shown the operational aspects 10 of a CT scanner and associated coordinate systems. In this example, a clinical CT scanner with a curved detector 12 is shown operating in helical scanning mode. In helical mode, the object is intentionally translated along the z axis at a constant rate at the same time as the source and detector rotate in a circle around the object to create a helical orbit. The method described here is equally applicable to helical or non-helical data. It is possible to define a world coordinate system $c'=(x, y, z) \in \mathbb{R}^3$ 14, which is fixed with respect to the scanner, its z-axis coinciding with the rotation axis of the scanner. Detector coordinate system $c=(u, v, z') \in \mathbb{R}^3$ 13 is fixed with respect to the rotating source-detector system 12: Its origin 13 is in the center of the detector 12, z' is parallel to z, u is tangent and v is orthogonal to the detector.

For motion correction it is necessary to know the motion of the object from view to view during the CT scan, in the world coordinate system, c'. Any rigid motion in the world coordinate system can be described by 6 parameters as:

$$S_{world}=(\phi_x,\phi_y,\phi_z,t_x,t_y,t_z)^T \qquad (1)$$

where $\phi_x$, $\phi_y$, $\phi_z$, are the rotations, and $t_x$, $t_y$, $t_z$, are the translations with respect to the x, y and z axes of the world coordinate system. The motion can be mapped into the detector coordinate system c as:

$$S_{detector}=(\phi_u,\phi_v,\phi_{z'},t_u,t_v,t_{z'})^T \qquad (2)$$

where $\phi_u$, $\phi_v$, $\phi_{z'}$, are the rotations, and $t_u$, $t_v$, $t_{z'}$, are the translations with respect to the u, v and z' axes in the detector coordinate system. A small motion $t_v$ in the direction perpendicular to the detector results in a very small magnification of the projection, which can usually be assumed negligible. In every projection view, then, one can set $t_v$ to zero and only 5 parameters need to be estimated in the correction scheme: $\phi_u$, $\phi_v$, $\phi_{z'}$, $t_u$ and $t_{z'}$.

$$S_{detector}=(\phi_u,\phi_v,\phi_{z'},t_u,t_{z'})^T \qquad (3)$$

The motion-corrected reconstruction requires the motion in the detector coordinate system, $S_{detector}$, to be converted to the world coordinate system. The motion described by $S_{detector}$ is converted to a homogeneous 4×4 transformation matrix, $T_{detector}$, which is then transformed to the world coordinate system with:

$$T_{world}=RT_{detector} \qquad (4)$$

where R is the 4×4 transformation matrix that maps the detector coordinate system to the world coordinate system.

B. Motion-Corrected Reconstruction

To correct for object motion, the reconstruction algorithm uses a source/detector orbit that has been modified, using knowledge of the motion, into the orbit that would have had to be followed, if the object remained stationary, to obtain the measured projections. This orbit is created by applying the inverse of the object's motion to the true detector orbit at all angles. A reconstruction algorithm with the ability to reconstruct from projections acquired along an arbitrary orbit is required. One such algorithm is Ordered Subset Expectation Maximization (OSEM). The OSEM-algorithm can be used for convenience, but if the use of a better noise model would be required, it can be replaced with, for example, a dedicated iterative algorithm for transmission tomography. Any analytical reconstruction algorithm capable of dealing with the motion, such as the Feldkamp-Davis Kress (FDK) algorithm (ref. J. Opt. Soc. Am. A1, 612-619, 1984), can also be used.

C. General Motion Correction Scheme

Turning to FIG. 2, there is illustrated a flow chart 20 of the method of the data-driven motion correction algorithm of this embodiment. The motion estimation 23 and the motion-corrected reconstruction 24 are alternately updated to increase the likelihood, and the iterations are stopped when the motion estimate appears to have converged 22.

The implementation involves: (1) a 2D-3D image registration 23 to update the pose estimate for each view at the current iteration; (2) an image update 24 using the changes of pose (motion) from view to view obtained in the previous step; (3) alternate updates of both image and motion with a multi-resolution scheme (FIG. 2, reference numbers 27 & 28) that increases the sampling as the number of iterations increases; (4) final motion-corrected reconstruction 25 of the desired image size performed as in [0028] above, assuming a source/detector orbit based on the last motion estimate.

1) Motion Update 23

From the measured raw data an initial image is reconstructed. This image can be a reconstruction produced with the system software (postprocessed to convert Hounsfield units back to attenuation integrals), or a first reconstruction (Eq. 5) from the measured data using any suitable iterative or analytical reconstruction algorithm.

For one projection line i, we integrate along the projection line to define the forward projection, $f_i$, of the current motion-corrected image estimate $\mu$. The index j indicates the voxel index, $\mu_j$ is the attenuation value at voxel j, and $a_{ij}$ is the sensitivity of projection bin i for activity in voxel j:

$$f_i = \sum_j a_{ij} \mu_j \tag{5}$$

The line integrals are organized in views, where view $\theta$ contains all line integrals associated with a single source position:

$$f_\theta = \{f_i\} \tag{6}$$

For each view, the 5 (or 6) motion parameters are estimated one after the other. Suppose the general motion correction scheme (FIG. 2) is at the iteration n, hence the current estimate of the motion parameters s at view $\theta$ is given by $s_\theta^n$. Let r be one of the parameters (a rotation or translation) to be estimated. Assuming that the change in the pose parameter represented by $\hat{r}\hat{s}$ is small, the derivative of projection f with respect to r can be approximated as a finite difference of the intensities:

$$\frac{\partial f_\theta}{\partial r} \approx \frac{f_{\theta,m} - f_\theta(s_\theta^n)}{\hat{r}} \tag{7}$$

where $f_\theta(s_\theta^n)$ is the calculated re-projection (using the current estimates for the image and motion) and $f_{\theta,m}$ is the measured projection for view $\theta$.

Figure 3:
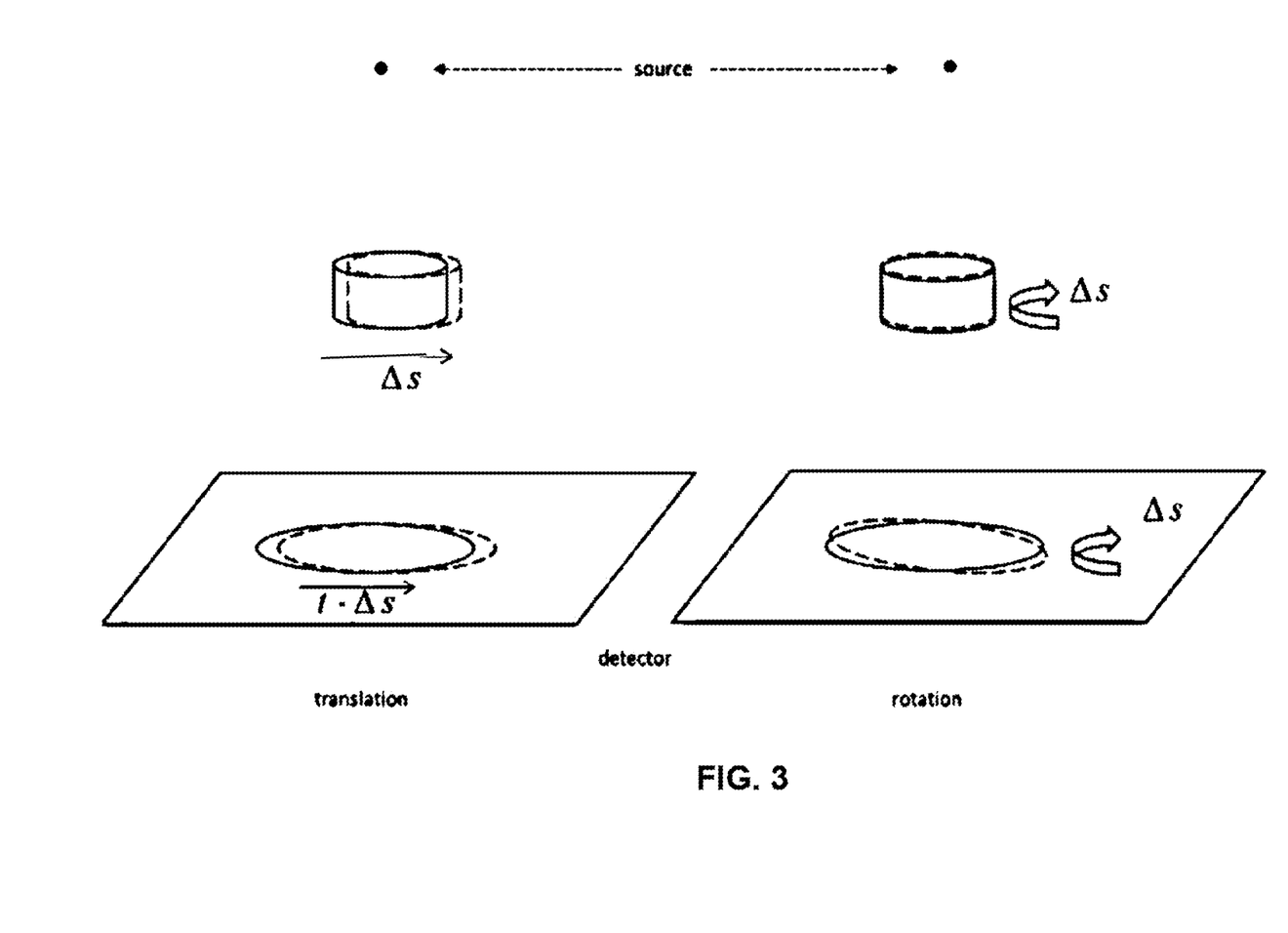
FIG. 3 illustrates schematically that the effect of object translation or rotation parallel to the detector can be well approximated as translation and rotation of the projection. For simplicity, the curvature of the detector was ignored. t is the magnification factor from the object to detector. However, for the two other rotations, more complicated calculations are required to compute their effect on the projection.

To estimate $\hat{r}$ in Eq. 7, it is necessary to know the derivative on the left hand side, hence another equation is introduced which is very similar to Eq. 7:

$$\frac{\partial f_\theta}{\partial r} \approx \frac{f_\theta(s_\theta^n + \Delta r) - f_\theta(s_\theta^n)}{\Delta r} \tag{8}$$

where $\Delta r$ is a known small increment of the parameter to be estimated. When $\Delta r$ represents a translation, $f_\theta(s_\theta^n + \Delta r)$ can be approximated as a simple translation of the current reprojection $f_\theta(s_\theta^n)$; for in-plane rotation, again $f_\theta(s_\theta^n + \Delta r)$ can be computed as a simple rotation of the re-projection $f_\theta(s_\theta^n)$, as shown in FIG. 3. For the two out-of-plane rotations, $f_\theta(s_\theta^n + \Delta r)$ is calculated with a forward projection of the object transformed by motion equivalent to $(s_\theta^n + \Delta r)$ in the world coordinate system. Eq. 7 and 8 assume that a small increment of one degree of freedom rigid motion only results in a linear change of the intensities in the projection. All the above lead to a least squares minimization problem for view $\theta$ at the current iteration, n:

$$\hat{r} = \arg\min_r \|\Delta r[f_{\theta,m} - f_\theta(s_\theta^n)] - r[f_\theta(s_\theta^n + \Delta r) - f_\theta(s_\theta^n)]\|^2 \tag{9}$$

To find $\hat{r}$, Eq. 9 is solved analytically. Defining $$P_\theta = f_{\theta,m} - f_\theta(s_\theta^n)$$

$$Q_\theta = f_\theta(s_\theta^n + \Delta r) - f_\theta(s_\theta^n) \tag{10}$$

and setting the derivative of the Eq. 9 with respect to r to zero, one obtains:

$$\hat{r} = \frac{\sum_N P_\theta Q_\theta}{\left\|\sum_N Q_\theta^2\right\|} \cdot \Delta r \tag{11}$$

where N is total number of voxels in one projection view $\theta$.

This procedure can be applied to estimate all five parameters in Eq. 3. The sequence of the estimation is translation first, then rotation. The newly estimated parameter values are used immediately when estimating the value of the next parameter. This sequential estimation of the five motion parameters for all projection views completes the update of the rigid motion in the current iteration. The rigid motion parameters for each projection view are obtained in the detector coordinate system (FIG. 1). They are then converted to a 4×4 transformation matrix representation, $T_\theta^{n,inc}$, and transformed to the equivalent transformation in the world (scanner) coordinate system, c', using Eq. 4, as required for the creation of the modified orbit.

The transformation matrix obtained in the current iteration (n) is then used to update the previous motion estimate for every view, which will be used in the next iteration (n+1):

$$T_\theta^{n+1} = T_\theta^n \cdot \Delta T_\theta^{n,inc}, \theta = 0, 1, \ldots, M. \tag{12}$$

2) Image Update 24

After obtaining the motion, the motion-corrected image can be updated with a suitable reconstruction algorithm such as OSEM, a dedicated iterative algorithm for transmission tomography, or an analytical algorithm capable of dealing with motion.

Rigid motion correction is done by performing reconstruction of the CT image while treating the acquired projections as having been acquired with an orbit given by the superposition of the inverse of the object motion and the true source/detector trajectory [3]. This required the introduction of a modified version of the standard reconstruction algorithm. For example, using OSEM, we have:

$$\hat{T}_i^{n+1} = \text{invert}(T_i^{n+1}) \tag{13}$$

$$\mu_j^{n+1} = \frac{\mu_j^n}{\sum_{i \in S_b} \hat{T}_i^{n+1}(a_{ij})} \sum_{i \in S_b} \hat{T}_i^{n+1}(a_{ij}) \frac{f_i}{\sum_k \hat{T}_i^{n+1}(a_{ik})\mu_k^n}$$

where i is the projection line index, j is the voxel index, $a_{ij}$ is the effective intersection length of line i with voxel j, f is the log converted projection, $S_b$ is one subset of projections of b subsets. $\hat{T}_i$ is a 4×4 rigid transformation matrix applied to the projection line i. The system matrix $a_{ij}$ is determined by the detector orbit. If $T_i$ is the identity matrix for all projection lines, then Eq. 13 is the same as conventional OSEM. In CT, $T_i$ is constant for all projection lines in one projection view. When the rotation speed is high and the number of views is large, the motion within a single view is negligible. In one example, the distance-driven projector was used for interpolation during the (back) projection. The new estimation of the motion-corrected image resulting from the image update can then be used for next motion update step.

3) Multi-Resolution Alternate Updates

By repeating the motion update and image update in turn, one can estimate the reconstruction (Eq. 13) and motion (Eq. 12) alternately. Because the motion-corrected image and the view-to-view motion are jointly estimated from the measured data, the problem of error propagation is mitigated.

An approach to reduce the computation time is to apply multi-resolution techniques. The embodiments utilize this technique by running the algorithm with a coarse to fine representation of the raw data and the image. As in FIG. 2, the image update can be reconstructed at coarse resolution at early iterations, with the resolution increasing as the iteration numbers increase (27, 28 of FIG. 2). Similarly, the projections in Eq. 5 can be computed with gradually increased resolution. A possible additional advantage of the multi-resolution scheme is that it may help to avoid convergence to an undesired local maximum. Since the computations at the finest resolution are the most expensive ones in the multiresolution scheme, in one example, the iterations were stopped at the one but finest resolution.

As proposed in an article published by J.-H. Kim et. al in the Journal of Physics in Medicine and Biology, the motion estimates can be smoothed (by filtering each component independently) to remove outliers. A Savitzky-Golay filter [20] can be applied after every motion update. It is found that, with an appropriate selection of the kernel size, this filter can achieve satisfactory jitter suppression in simulations and patient scans. The optimal kernel size depends on the number of CT projections acquired during each source/detector rotation and the axial detector extent.

It is not obvious how to define good stopping criteria for the motion estimation, especially considering that a ground truth image is unavailable for clinical data. In the motion estimation scheme, a maximum number of iterations is chosen for each resolution level. In addition, the summation of projection errors between the re-projected and measured data over all the views is computed, and at each resolution level, the iterations are stopped earlier when the relative change of this error measure is less than some fraction (e.g. 5%) of the summed error between the last re-projected and measured data.

4) Final Reconstruction 25

When the motion estimate has converged, a final reconstruction of the desired image size is produced. In diagnostic CT imaging, for example, the image size will normally be chosen to match the conventional reconstruction. This may be started with the last image update from the alternate updates as the initial estimate, or as we have done in diagnostic helical CT, it can be started from an approximate helical Feldkamp-Davis-Kress reconstruction (with motion correction enabled in the backprojection step) This approximation creates low frequency motion artifacts, but we observe that these are readily eliminated during subsequent reconstruction with an iterative algorithm such as OSEM.

To further accelerate the final reconstruction, the forward and backward projection operations may apply Nesterov's momentum approach [22] which uses all previous iterates to compute the momentum, and be implemented in a language supporting parallel processing, such as OpenCL, and run on a GPU (e.g. NIVIDIA Tesla C2075) or multi-core computer.

Experiments and Results

Simulation:

In the simulation of a diagnostic helical CT scan, a segment of measured head motion from a volunteer was applied to a voxelized phantom to generate a simulated scan. Reconstructions from this scan were analyzed quantitatively to assess the performance of the motion correction algorithm. The phantom was a 3D voxelized phantom from the Visible Human Project [20]. The units were converted from Hounsfield units (HU) to attenuation coefficients ($cm^{-1}$) at peak kilovoltage of 70 kVp. The image size was 256×256×240, pixel size was 1×1×1 $mm^3$. A helical scan with a Siemens Definition AS CT scanner (Siemens Medical Solutions USA, Inc., Malvern, Pa.) was simulated, with reduced angular sampling to reduce the computation times. The acquisition parameters were: angles per rotation 250, pitch 1.0, collimation 32×1.2 mm. The motion was applied to the phantom for the simulated helical scan. To avoid cone-beam artifacts, all simulated helical scans covered a bit more than the entire object.

Figure 4:
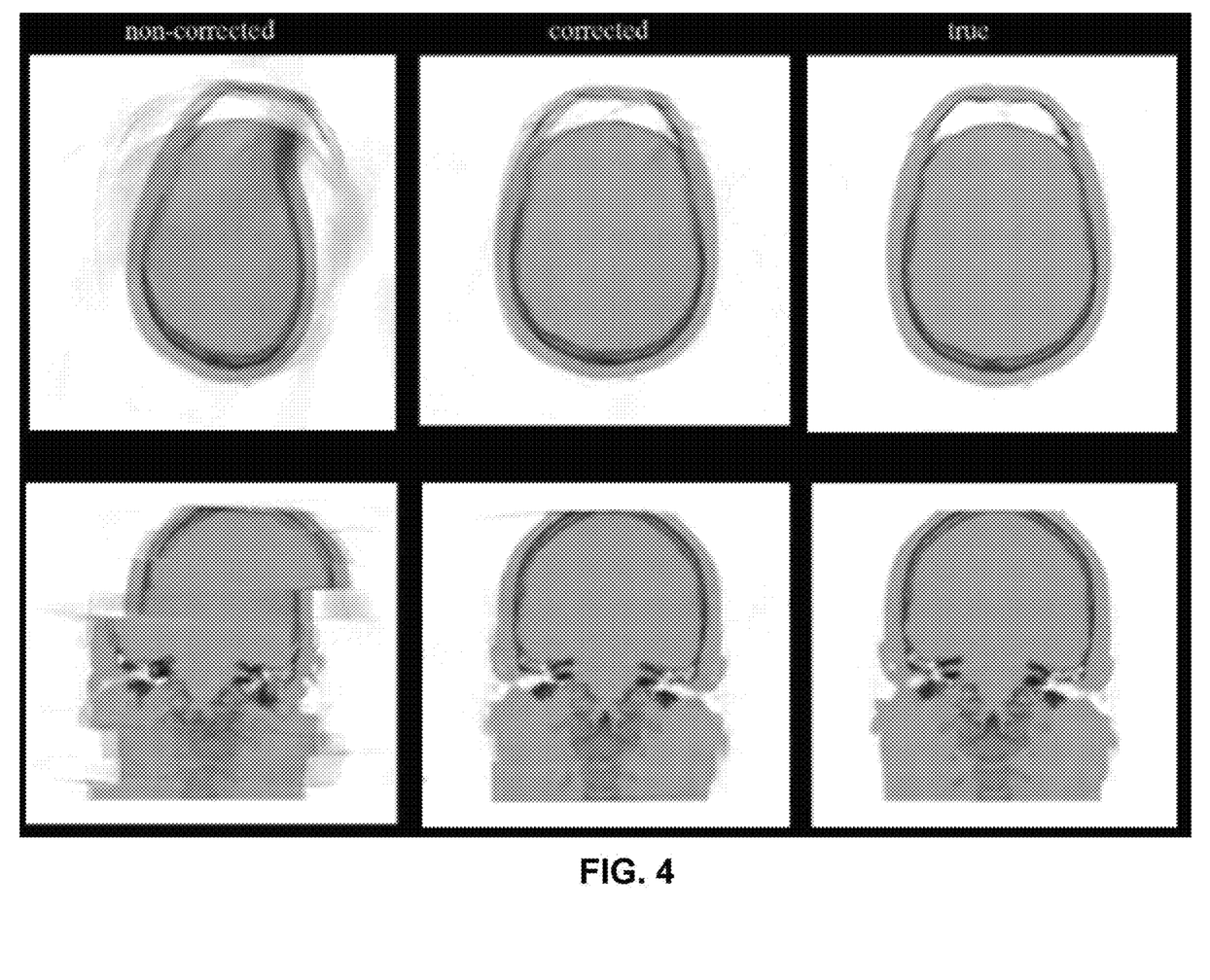
FIG. 4 illustrates selected transaxial and coronal slices from reconstructions without and with motion correction from a simulation experiment with motion, and also from the true image. The simulated motions were based on recorded motions from human volunteers.
Figure 5:
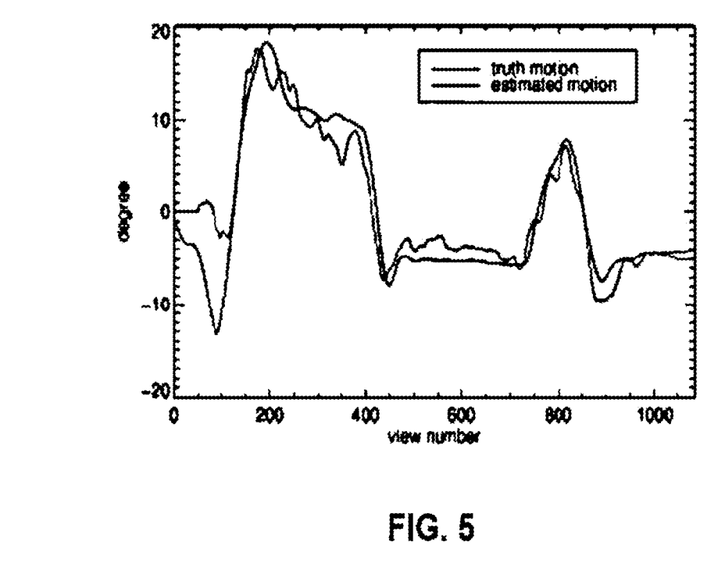
FIG. 5 and FIG. 6 are graphs of the estimated motion values as a function of the view angle for the two most prominent motion parameters, with FIG. 5 showing rotation about the scanner x coordinate axis, $\phi_x$, and FIG. 6 showing translation in the direction of the x axis, $t_x$.
Figure 6:
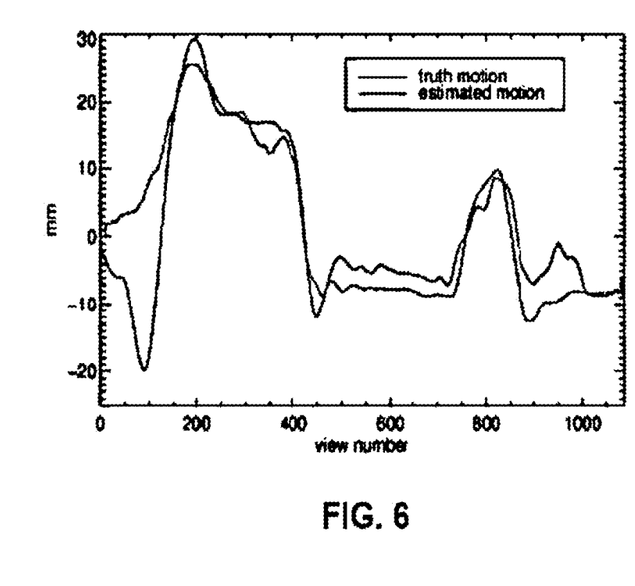

OSEM was used for all reconstructions, with motion correction enabled (Eq. 13). During the joint estimation of the motion-corrected image and the motion, the motion-corrected image was updated using 1 OSEM iteration with 40 subsets. Reconstruction pixel size was 1×1×1 $mm^3$ at the finest resolution. Alternate updates of both image and motion were performed within a multi-resolution scheme to obtain the optimal motion. For the final reconstruction, 4 iterations and 60 subsets were applied. FIG. 4 shows, for one representative transaxial slice (top row) and one representative coronal slice (bottom row), a comparison of the reconstruction obtained without motion correction using the conventional reconstruction method (left column), the motion-corrected reconstruction (middle column), and the true image (right column). There is very good correspondence between the motion-corrected image and the true image. All images inverted for reproduction FIG. 5 and FIG. 6 are graphs of the estimated motion values as a function of the view angle for the two most prominent motion parameters, with FIG. 5 showing $\phi_x$, and FIG. 6 showing $t_x$.

Real Scan:

The method was applied to clinical studies in which motion artifacts had been observed. The outcome was evaluated by assessing the image visually. The anonymized raw data of one patient who had previously undergone a head CT scan in the Department of Radiology at Westmead Hospital, Sydney, Australia, were collected with the approval of the Human Research Ethics Committee of the Western Sydney Local Health District. The scan was performed on a Siemens Force scanner (pitch 0.55, tube voltage 120 kVp, tube current 150 mAs, angles per rotation 1050, collimation 64×0.6 mm). Flying focus was turned on in both z and phi directions.

Figure 7:
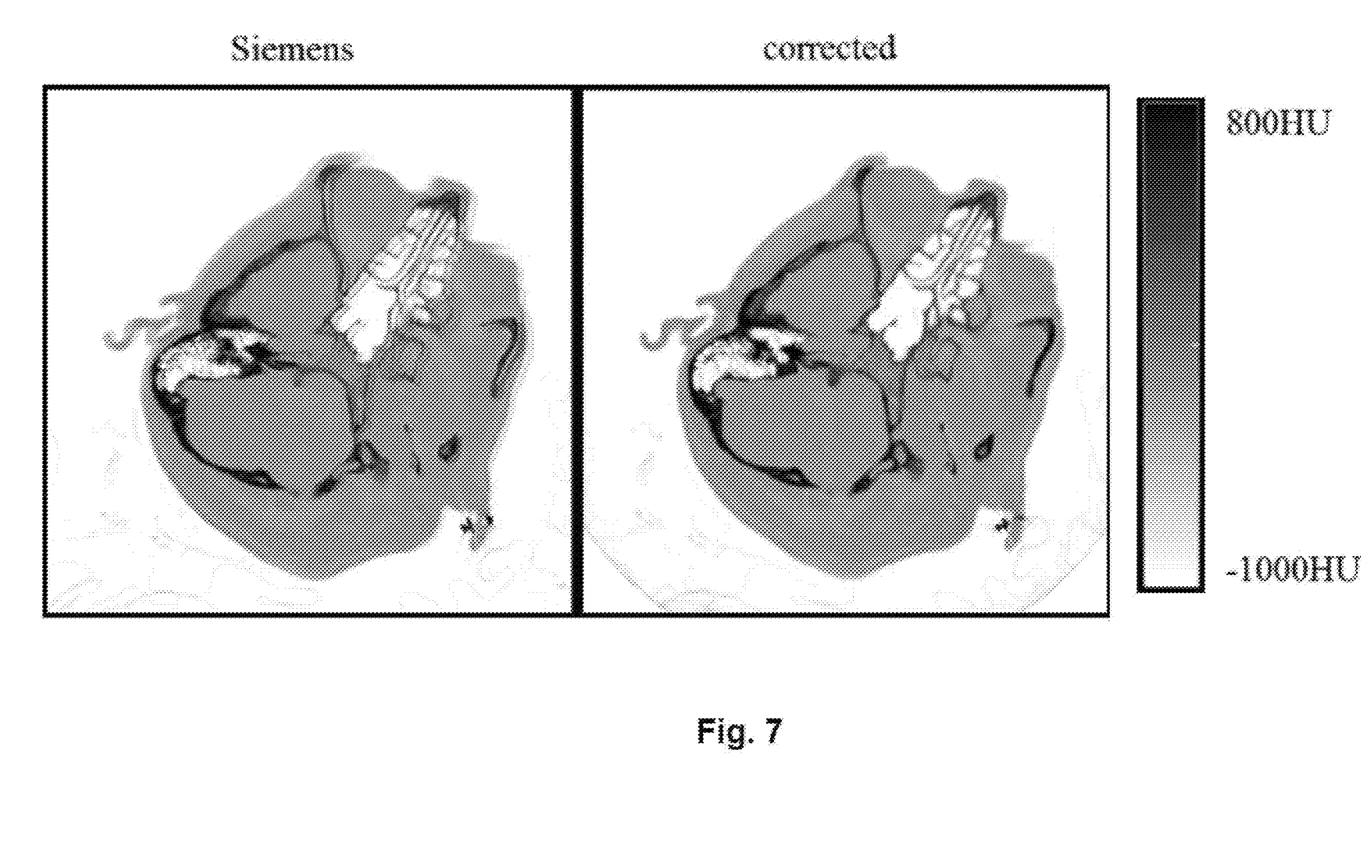
FIG. 7 shows a selected transaxial plane, without (left) and with correction (right) for motion artifacts in a clinical CT scan.

To reduce the amount of computation required for the motion updates and the image updates, the number of projections was reduced by a factor of 8 by taking the average of every 8 projections OSEM was used as the reconstruction algorithm. The motion correction was enabled for all reconstructions. Unlike in the simulation, 2 OSEM iterations with 40 subsets were performed for the image updates. The final reconstruction pixel size was 0.40039×0.40039×0.75 mm$^3$, image size was 512×512×436. To further accelerate the motion estimation, the multi-resolution scheme was applied as described above. Stopping criteria are also described above. For the final reconstruction with motion correction, the starting image was obtained as described above using an approximate motion-corrected FDK reconstruction. Six OSEM iterations with 60 subsets were applied in combination with Nesterov's acceleration [22] on the GPU. FIG. 7 shows (inverted views of) the original reconstructed image produced by the CT vendor software (left) and the final reconstruction (right) produced by our method with the same image size. Ghost artifacts are visible in the vendor's reconstruction that do not appear in the final reconstruction.

The forgoing described embodiments provide a motion estimation and correction approach for X-ray CT of rigid objects (e.g., the head and other rigidly moving body parts in medical CT imaging) based only on the measured raw data. Since no additional measurements are needed, it can be applied retrospectively to any previously acquired CT data.

Interpretation

Reference throughout this specification to "one embodiment", "some embodiments" or "an embodiment" means that a particular feature, structure or characteristic described in connection with the embodiment is included in at least one embodiment of the present invention. Thus, appearances of the phrases "in one embodiment", "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

As used herein, the term "exemplary" is used in the sense of providing examples, as opposed to indicating quality. That is, an "exemplary embodiment" is an embodiment provided as an example, as opposed to necessarily being an embodiment of exemplary quality.

It should be appreciated that in the above description of exemplary embodiments of the invention, various features of the invention are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those skilled in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

What is claimed is:

1. A method for a reduction of motion artifacts in computed tomography (CT) reconstruction imagery, the method including the steps of:

(a) reconstructing, from a CT data set comprising measured projections acquired by a detector at a plurality of angles around an object of interest, an initial estimate of a 3D attenuation distribution of the object of interest;

(b) at each angle of the CT data set, a forward projection of the estimated 3D attenuation distribution within the object of interest and the CT projection measured at the same projection at the same angle are used to estimate a pose of the object of interest;

(c) undertaking a further reconstruction from the measured projections, accounting for a pose changes between two successive pose estimates from (b) to produce a motion corrected estimate of the 3D attenuation distribution;

(d) iterating steps (b)-(c) until the pose estimates obtained at all angles in two successive iterations differ by less than a predetermined convergence criterion; and (e) producing a final image reconstruction of a desired image size using a final pose estimates obtained at an end of step (d).

2. The method as claimed in claim 1, wherein said steps (b) and (c) include the minimization of a cost function including a summation of differences between the measured projections and the corresponding forward projections of the motion corrected estimate of the 3d attenuation distribution at all projection angles.

3. The method as claimed in claim 1, further comprising performing the method across multiple resolutions of the CT data set and image by increasing a sampling of the CT data with further iterations of steps (b) to (c).

4. The method as claimed in claim 3, wherein the multiple resolutions provide an increasing resolution for successive estimates of the 3D attenuation distribution.

5. The method as claimed in claim 1, wherein the pose includes three dimensional rotation and translation of the object of interest.

6. A method according to claim 5, wherein a coordinate system for the pose is with respect to the detector.

7. The method as claimed in claim 6, wherein one of said translations is perpendicular to the detector and the perpendicular translation is neglected in the pose estimate.

8. The method as claimed in claim 1, wherein said step (c) includes applying an ordered subset expectation maximization (OSEM) image reconstruction algorithm to the measured projections of the CT data, making use of the pose changes to estimate an arbitrary orbit used in the OSEM.

9. A method according to claim 1, wherein the computed tomography (CT) includes at least one of helical CT, circular orbit CT, cone beam CT and dental CT.

10. A method according to claim 1, wherein said step (c) includes applying an image reconstruction algorithm that makes use of the pose changes to estimate a modified orbit to obtain a motion corrected image reconstruction from the measured CT projections, or applying an ordered subset expectation maximization (OSEM) that makes use of the pose changes to estimate a modified orbit to obtain a motion corrected image reconstruction from the measured CT projections.

* * * * *